United States Patent [19]

Kjems

[11] Patent Number: 5,393,535
[45] Date of Patent: Feb. 28, 1995

[54] ORALLY ADMINISTERABLE CALCIUM SUPPLEMENT FOR CATTLE

[76] Inventor: Gunnar Kjems, Peter Hvitfeldts Strade 12, 1173 Copenhagen K., Denmark

[21] Appl. No.: 761,364
[22] PCT Filed: Feb. 27, 1990
[86] PCT No.: PCT/DK90/00055
§ 371 Date: Oct. 25, 1991
§ 102(e) Date: Oct. 25, 1991
[87] PCT Pub. No.: WO90/09797
PCT Pub. Date: Sep. 7, 1990

[30] Foreign Application Priority Data
Feb. 27, 1989 [DK] Denmark .................... 0926/89

[51] Int. Cl.⁶ .................. A01N 59/08; A01N 59/06
[52] U.S. Cl. ............................ 424/678; 424/438; 424/681; 424/682; 424/683; 424/686; 424/688; 424/692; 424/697; 424/715; 424/717; 426/73; 426/534; 426/602; 514/937; 514/938; 514/943; 514/557; 514/474
[58] Field of Search ............ 424/678, 682, 686, 687, 424/689, 693, 438, 681, 683, 688, 692, 697, 715, 717; 426/73, 602, 534; 514/937, 938, 943

[56] References Cited

U.S. PATENT DOCUMENTS

| | | | |
|---|---|---|---|
| 2,198,165 | 4/1940 | Hamburger | 514/557 |
| 3,461,203 | 8/1969 | Ringarp et al. | 424/153 |
| 4,259,323 | 3/1981 | Ranucci | 514/943 |
| 4,650,690 | 3/1987 | Bams et al. | 426/605 |

FOREIGN PATENT DOCUMENTS 334766  3/1921  Germany.

OTHER PUBLICATIONS

Remington's Pharmaceutical Sciences, 15th edition, 1975, Easton (Pa.), Mack Publishing Company, pp. 327–331.
Jonsson, G., The Veterinary Record (1978), 102, 165–169.

*Primary Examiner*—Allen J. Robinson
*Assistant Examiner*—John D. Pak
*Attorney, Agent, or Firm*—Michael L. Dunn

[57] ABSTRACT

A calcium ion containing composition comprising a water in oil emulsion having a dispersed aqueous phase and a continuous oil phase, which composition is orally administerable and palatable to cows without causing lesions of the stomach and which composition is effective in preventing milk fever, said composition further comprising a calcium salt which is dissolved in the aqueous phase to form a calcium ion containing aqueous phase solution, the calcium in the composition, calculated as free calcium ion, comprising 10 to 20 percent by weight of the composition, said composition further including from 0.5 to 10 percent oil soluble non-ionic emulsifier. The invention also includes the method of orally administering the composition to cows to treat milk fever.

6 Claims, No Drawings

ORALLY ADMINISTERABLE CALCIUM SUPPLEMENT FOR CATTLE

The present invention concerns an orally administerable composition for prevention and treatment of calcium deficiency in cattle, e.g. milk fever, said composition containing as active component a readily absorbable calcium compound.

Milk fever is a disease which is particularly caused by a strong decline in the Ca content of the blood in the period immediately up to calving and at the beginning of lactation. The predominant part (about 75%) of the incidences occur during the first 24 hours after calving (M. Dantzer, Dansk Vet. Tidsskr. 1987, 70, 4 15/2, p. 148-154). The disease is normally treated by intravenous injection of calcium, in particular in the form of calcium borongluconate.

In Denmark 4-6% of first-time parturitions are complicated by milk fever, but in Sweden the figure is even higher, about 8%, cf. G. Jonsson, The Veterinary Record, (1978), 102, 165-169. However, there are considerably variations between the herds, depending upon race, yield, average age and feed composition.

Cows which have once suffered from milk fever are particularly predisposed to acquire the disease again at the time of subsequent parturitions, and the disease occurs frequently in older cows (Dantzer, op. cit.).

A preferred method, cf. G. Jonsson op. cit., to prevent milk fever is short term oral administration of readily absorbed calcium salts. The rapid absorption of calcium from a calcium chloride solution has been demonstrated by i.a. Hallgren, Wien. Tierärztl. Mschr. 52 (1965), p. 359-369, whose preliminary experiments showed a good preventive effect. However, the bitter taste and locally irritating effect of calcium chloride entail that the cows are extremely unwilling to take the solutions, which involves a risk of aspiration and consequent aspiration pneumonia, etching of lung and dead. A stomach probe was therefore used in Hallgren's experiments so that the solution was administered directly in the stomach.

It goes without saying that this method is not feasible as a general prevention without veterinary assistance.

To remedy these drawbacks, $CaCl_2$ in the form of viscous liquids have been used for several years. Since cows cannot spit, they generally have no alternative but to swallow liquids which are so viscous that they do not run out of the mouth.

A commercially available product contains $CaCl_2$ and MgO in a viscous solution. This product is not taken willingly by the cows and therefore involves a risk of aspiration.

The aspiration problem can be reduced additionally by mixing calcium chloride in gels on the basis of water and inert cellulose derivatives, such as hydroxyethylcellulose or ethylcellulose. The U.S. Pat. No. 3,461,203 reports experiments where water-free $CaCl_2$ in amounts of 232, 115 and 100 were mixed with 9-10 g of hydroxyethylcellulose and water up to 450-400 ml. These gels were administered daily for 5-10 days, of which two days were post partum. The milk fever incidence was reduced by from about 50% in the control groups to about 10% in the treated groups. According to G. Jonsson, op. cit., the drawbacks of this method are the difficulty in predicting calving with sufficient accuracy, just as the farmers regard the method as very laborious, in particular because of the resistance of the cows.

In view of this Jonsson and associates shortened the gel treatment, but still administered 150 g or 100 g of water-free $CaCl_2$ dispersed in hydroxy ethyl cellulose and water up to 450 ml leading to a reduction of the milk fever incidence from 46 to 23%.

However, Jonsson concluded that even though gel intake is relatively convenient, voluntary intake of $CaCl_2$ would be better. Jonsson therefore disguised the bitter taste of $CaCl_2$ in a feed supplement, but obtained no preventive effect on milk fever, which he attributes to the fact that almost all cows cease eating on the day of calving or the day before.

Dantzer, op. cit., moreover states that $CaCl_2$ gels are acid and taken only unwillingly by the cows.

As mentioned more fully below, Jess Jørgensen et al., Dansk Vet. Tidsskr. 1990, 73, 3½, p. 140 reports examinations which show that $CaCl_2$ gels on the basis of hydroxyethylcellulose can have an etching effect on the stomach wall in cows.

Dantzer also examined the effect of the so-called calving lime which consists of 95% $CaHPO_4$ and 5% MgO as well as 96000 vitamin $D_3$ per dose.

Dantzer reports that the product is willingly taken perorally by the cows. MgO is added because many cows suffer from hypomagnesemaemia, which makes them predisposed to milk fever. Dantzer's conclusion to the admittedly limited test material is that calving lime is less effective than $CaCl_2$ gel. The reason is presumably the limited solubility of $CaHPO_4$ and the consequent limited calcium absorption.

Thus, there is still a need for a calcium based composition which effectively prevents milk fever, which is taken willingly by the cows, and which is not vitiated by any risk of aspiration upon oral intake.

The invention is based on the surprising finding that the troubles can be remedied by the use of calcium compounds, in particular calcium chloride, if the calcium compound is suspended or emulsified in an oil phase.

In view of this the invention concerns an orally administerable composition for prevention or treatment of milk fever in cattle, said composition containing as active ingredient a readily absorbable calcium compound, the composition being characterized in that the calcium compound is suspended or emulsified in an oil phase.

As explained by Hallgren and Dantzer, op. cit., the total calcium content in serum consists of a diffusable portion (about 55%) in equilibrium with a protein bonded portion (about 45%). The diffusable portion, which is the readily useful portion, consists of about 45% free calcium ions and about 10% complex bonded calcium. This equilibrium is pH dependent and is shifted towards free calcium ions with a declining pH.

Since only the ionized calcium ($Ca^{++}$) is absorbed from the intestine of the cow, the constituent calcium compound must therefore be water soluble, and to make the pH of the serum go in an acidic direction salts having an acidosing (acidotic) effect, such as calcium chloride, are preferred.

Also other soluble calcium salts are useful, such as calcium formate, calcium acetate, calcium propionate, calcium gluconate, calcium borongluconate, calcium lactate, calcium laevulate, and calcium ascorbate.

The oil phase is formed by an edible oil. Preferred oils are vegetable oils, such as soybean oil, repeseed oil, olive oil, groundnut oil, apricot kernel oil, grapeseed oil, almond oil, linseed oil, peach kernel oil, palm oil, coconut oil, castor oil, sunflower oil and corn oil. Also animal oils, such as fish oils, can be used.

As mentioned, the composition of the invention is characterized in that the calcium compound is suspended or emulsified in an oil phase.

Based on weight, the composition may thus comprise 0–80%, in particular 0–70% water phase, and 100–20%, in particular 100–30% oil phase. The preferred mixing ratio is 40–70% water phase and 60–30% oil phase.

The content of calcium calculated as free $Ca^{++}$ in the finished mixture is 1–25% by weight, preferably 10–20%.

It could not be expected in advance that it would be possible to formulate emulsions with such a high content of dissolved calcium compound in such a large amount of water phase, i.a. because of the increased density and increased ion strength of the water phase.

In the preferred embodiment, the calcium compound is thus dissolved in the aqueous phase in a water-in-oil emulsion. To ensure suitable emulsion stability, the emulsion contains one or more emulsifiers. Suitable emulsifiers are e.g. oil soluble non-ionic emulsifiers, in particular esters of polyvalent alcohols, preferably glycerol, with fatty acids or polymerized oils.

It has been found that a particularly good emulsion stability may be obtained with polyglycerol esters of polymerized soybean oil.

The concrete emulsifier selection and emulsifier amount depend i.a. upon the ratio of water phase to oil phase, the type of the oil phase and the amount of dissolved calcium compound.

The most expedient emulsifier and emulsifier amount can thus be found by experiments.

The emulsifier is used in an amount of 0.5–10%, calculated on the finished mixture, in particular 1–4%, preferably 1.5–2.5%.

The composition of the invention may moreover contain additives such as mineral supplements, e.g. magnesium or selenium, vitamin D and flavouring substances, sweetening agents, antioxidants and preservatives. If desired, thickeners may moreover be added to one or both phases.

To produce the present composition in the form of an emulsion, the calcium compound is dissolved in water together with optional preservatives and thickeners and is heated to about 50° C. This solution is mixed with an about 50° C. hot solution of emulsifier and optional antioxidants, sweetening agents and flavouring substances in the oil used with vigorous stirring. The resulting emulsion may be homogenized if desired.

The suspension may be produced analogously, however without addition of water.

The desirable peroral dose is 50 g of free $Ca^{++}$ which is administered in prophylactic treatment 24 hours before expected calving, immediately after calving as well as 12 and 24 hours later.

Peroral treatment is also used as a supplement to intraveneous calcium treatment and is then dosed with 50 g of $Ca^{++}$ 4, 12 and optionally 24 hours after the intraveneous treatment.

A composition according to the invention may e.g. be composed as follows:

| | |
|---|---|
| $CaCl_2$, Pharmacopea Nordica | 25% |
| Soybean oil | 47% |
| Emulsifier | 3% |
| Water | 25% |
| Flavouring substances | 0.04% |

| | |
|---|---|
| (coconut and vanilla) | |
| Saccharine sodium | 0.01% |
| Antioxidant | |
| Preservative | |

A typical composition may consist of:

| | |
|---|---|
| $CaCl_2$, $6H_2O$ | 300 g (corresponding to 50 g of $Ca^{++}$) |
| Water | 100 g |
| Emulsifier | 16 g |
| Soybean oil | 380 g |
| Additives | 4 g |
| | 800 g |

The commercially available products "Calol ®" and "KOVEL ®" respectively contain

| | | |
|---|---|---|
| $CaCl_2$, $2H_2O$ | 200 g | 200 g |
| Soybean oil | 280 g | 380 g |
| Water | 200 g | 200 g |
| Auxiliary substances and flavour | 20 g | 20 g |
| | 700 g | 800 g |

The composition of the invention is being tested in a large number of herds.

Initial experiments have shown that the cows willingly take the composition. The composition has till now been tested as a supplement for intravenous administration of calcium borongluconate in confirmed milk fever incidences, where $CaCl_2$ gel as well as placebo control were used for comparison. 8 g of $Ca^{++}$ were administered intraveneously, as well as 8 g of $Ca^{++}$ subcutaneously for precipitation in three groups of ten cows, where two groups were subsequently treated with 50 g of $Ca^{++}$ either as Calol ®/KOVEL ® or as $CaCl_2$ gel. The third group served as control.

Both oral treatments showed significant effects on the clinical symptoms. In terms of effect, there was no difference between Calol ®/KOVEL ® and the gel, but Calol ®/KOVEL ® was accepted much better by the cows and were much easier to administer. The test will be reported at the XVI World Buiatrics Congress, Bahia, Brazil, Wermuth et al. "New Treatment of Milkfever".

Jess Jørgensen et al., Dansk Vet. Tidsskrift, 1990, 73, 3 ½, p. 140 refers to comparitive examinations between $CaCl_2$ gels with hydroxyethylcellulose as gel former and a composition according to the invention in the form of an emulsion in 380 g of soybean oil. Both compositions contained 400 ml, 49% aqueous $CaCl_2$, $H_2O$.

It was concluded that the gel composition in the dose used can cause pronounced clinical and pathological side effects, in particular by way of lesions of the stomach wall while the composition of the invention only involved relatively mild clinical symptoms and superficial or no pathological lesions.

In a further examination by the National Institut of Animal Science, Ole Aaes "Report on the influence of various culture calcium compositions on feed intake when feeding according to appetite" it was demonstrated that, in addition to the above-mentioned lesions on the stomach wall, the $CaCl_2$ gels also reduced the appetite. Thus, feed intake measured as kg dry matter was reduced by 2.8 feed units (FU), while Calol ®

/KOVEL ® only reduced the feed intake by 2.1 FU. However, to this should be added that about 3.2 FU were added with the soybean oil, which will give an unchanged or positive energy balance even with a digestibility of about 75%.

I claim:

1. A method for treating milk fever in cows which comprises orally administering to cows in need thereof an effective amount of a calcium ion containing composition comprising a water in oil emulsion having a dispersed aqueous phase and a continuous oil phase, which composition is orally administerable and palatable to cows, said composition further comprising calcium chloride which is dissolved in the aqueous phase to form a calcium ion containing aqueous phase solution, the calcium in the composition, calculated as free calcium ion, comprising 10 to 20 percent by weight of the composition, said composition further including from 0.5 to 10 percent emulsifier; wherein said composition is orally administered in a plurality of doses within 24 hours before and 24 hours after calving to provide a total of at least 150 g of free $Ca^{++}$ ion.

2. The method of claim 1 wherein said emulsion includes from 40 to 70 percent aqueous phase and 30 to 60 percent oil phase.

3. The method of claim 1 wherein the emulsifier is an ester of a polyvalent alcohol with a fatty acid or of a polymerized oil.

4. The method of claim 1 wherein the emulsifier is a polyglycerol ester of polymerized soybean oil.

5. The method of claim 1 wherein the oil phase consists of an edible oil selected from the group consisting of soybean oil, rapeseed oil, groundnut oil, and grapeseed oil.

6. The method of claim 1 wherein the composition further contains additives selected from the group consisting of magnesium salts, vitamin D, flavorings, sweeteners, antioxidants, and preservatives.

* * * * *